United States Patent [19]

Miller et al.

[11] Patent Number: 4,694,082
[45] Date of Patent: Sep. 15, 1987

[54] COMPOUND 1,4-DIISOPROPYL-2,5-DIKETOPIPERAZINE

[75] Inventors: William H. Miller, Glendale; William D. Taylor, St. Louis, both of Mo.

[73] Assignee: Monsanto Company, St. Louis, Mo.

[21] Appl. No.: 778,818

[22] Filed: Sep. 23, 1985

[51] Int. Cl.$^4$ ............................................. C07D 241/08
[52] U.S. Cl. ..................................................... 544/385
[58] Field of Search ......................................... 544/385

[56]     References Cited
U.S. PATENT DOCUMENTS

| 3,927,080 | 12/1975 | Gaertner | 260/502.5 |
| 3,969,398 | 7/1976 | Hershman | 260/502.5 |
| 4,065,491 | 12/1977 | Pfliegel et al. | 260/502.5 |
| 4,140,791 | 2/1979 | Chan | 544/385 |
| 4,237,065 | 12/1980 | Ehrat | 260/502.5 |
| 4,400,330 | 8/1983 | Wong et al. | 544/337 |

FOREIGN PATENT DOCUMENTS 0055695  7/1982  European Pat. Off. .

OTHER PUBLICATIONS

Sut et al., "N-Monoalkylation of Some 2-Oxo and 2,5 Diketopiperazines", *Chimie Therapeutique*, 4 (3), 167–173 (1969).

Okawara et al., "Convenient Syntheses of Piperazine-2,5-Diones and Lactams from Halocarboxamides Using Phase Transfer Catalysts".

*Chemistry Letters*, 1981, pp. 185–188.

Cavicchioni et al., "Base-promoted Reactions of αHalogenoalkylanilides", *J. Chem. Soc. Perkin Trans. I*, pp. 2969–2972 (1982).

*Primary Examiner*—Glennon H. Holarah
*Assistant Examiner*—James H. Turnipseed
*Attorney, Agent, or Firm*—Frank D. Shearin

[57]              ABSTRACT

The novel compound 1,4-diisopropyl-2,5-diketopiperazine can be hydrolytically cleaved to prepare N-isopropylglycine, which can be reacted with formaldehyde and prosphorous acid to produce N-isopropyl-N-phosphonomethylglycine. The latter compound can be dealkylated in the presence of base to produce N-phosphonomethylglycine, a well known herbicide.

1 Claim, No Drawings

COMPOUND 1,4-DIISOPROPYL-2,5-DIKETOPIPERAZINE

BACKGROUND OF THE INVENTION

This invention relates to compositions useful as intermediates in the synthesis of herbicides. More particularly, the invention relates to 1,4-diisopropyl-2, 5-diketopiperazine, which has been found to be especially advantageous as an intermediate in the preparation of N-isopropylglycine, a precursor of the herbicide N-phosphonomethylglycine.

N-phosphonomethylglycine, known also by its common name glyphosate, is a highly effective and commercially important phytotoxicant useful in controlling a large variety of weeds and crops. It is applied to the foliage of a very broad spectrum of perennial and annual grasses and broad-leafed plants. Industrial uses include control of weeds along roadsides, waterways, transmission lines, in storage areas, and in other nonagricultural areas. Usually glyphosate is formulated into herbicidal compositions in the form of its various salts which retain the anionic form of glyphosate in solution, preferably in water.

Because of its commercial importance, many processes for making glyphosate have been published. One conventional process for the manufacture of glyphosate is described by Hershman in U.S. Pat. No. 3,969,398. In that process, iminodiacetic acid is reacted with formaldehyde and phosphorous acid to produce an intermediate N-phosphonomethyliminodiacetic acid. This intermediate is oxidized to produce glyphosate.

Another process for the manufacture of glyphosate is described by Gaertner in U.S. Pat. No. 3,927,080. Gaertner describes the production of glyphosate wherein N-t-butyl-N-phosponomethylglycine or its esters are hydrolyzed under acidic conditions. In the process of Gaertner, t-butylamine is reacted with a bromoacetate ester to produce an ester of N-t-butylglycine, which is in turn reacted with formaldehyde and phosphite esters to produce the esters of the N-t-butyl-N-phosphonomethylglycine intermediate.

European Pat. No. 0,055,695 discloses a process for splitting off a substituent group from the nitrogen atom of an N-substituted N-phosphonomethyl-glycine by hydrogenolysis. The N-substituent is described as a 1-arylalkyl group suitable for hydrogenolytic cleavage. The hydrogenolytic process is carried out in the presence of a catalyst such as platinum or palladium on barium sulfate.

Pfleigel et al U.S. Pat. No. 4,065,491 describes a process in which glycine is reacted with formaldehyde and a phosphite ester to produce an ester of glyphosate. Ehrat U.S. Pat. No. 4,237,065 describes a process generally similar to that of the Pfleigel patent.

In the copending and coassigned application of Miller et al, Ser. No. 687,404, filed Dec. 28, 1984, a process is described in which glyphosate is prepared by dealkylation of N-isopropylglyphosate. This has been found to be a particularly effective process for the preparation of glyphosate in relatively high yields. It has been determined, moreover, that the precursor N-isopropylglyphosate may be prepared by phosphonomethylation of N-isopropylglycine. Methods are known for the phosphonomethylation of N-alkylglycines by reaction with formaldehyde and phosphorous acid. The copending and coassigned application of Miller et al. Ser. No. 778,958, filed Sept. 23, 1985 describes a process in which an N-acetyl-N-alkylglycine is phosphonomethylated by introducing both formaldehyde and phosphorous acid into a single reaction pot, without any isolation of the product of the hydrolysis of the acetyl group. According to the latter process, the N-alkyglyphosate also can be dealkylated to glyphosate without prior isolation.

A need, therefore, exists for additional intermediates which can be effectively and economically converted to N-alkylglycines, most particularly N-isopropylglycine, as part of the synthesis of N-alkylglyphosates and glyphosate itself.

A variety of 1,4-disubstituted 2,5-diketopiperazines are known to the art, and are recognized to be useful for various purposes. Thus, for example, Chan et al U.S. Pat. No. 4,140,791 discloses the use of 1,4-di(2,6-dimethylphenyl)-2,5-diketopiperazine for control of various fungal diseases. Sut et al, "N-Monoalkylation of Some 2-Oxo and 2,5-Dioxopiperazines", *Chimie Therapeutique*, 4 (3), 167–173 (1969), describe the syntheses of a series of 2-oxopiperazines and 2,5-dioxopiperazines which were found to have analgesic and anesthetic activities. Among the specific compounds disclosed by Sut et al are 2,5-diketopiperazines and 3-substituted-2,5-diketopiperazines which are monoor dialkylated at an N- position, or N,N' positions, with ethyl, benzyl, hydroxyethyl, or acetoxyethyl. Other references contain specific disclosure of 1,4-dimethyl-2,5-diketopiperazine, 1,4-diethyl-2,5-diketopiperazine, 1,4-diphenyl-2,5-diketopiperazine, and 1,4-dibenzyl-2,5-diketopiperazine; but it is believed that none of these references disclose the use of such compounds in the preparation of glyphosate or glyphosate precursors.

Okawara et al, "Convenient Syntheses of Piperazine-2,5-Diones and Lactams from Halocarboxamides Using Phase Transfer Catalysts", *Chemistry Letters*, 1981, pp. 185–188 shows the syntheses of various 1,4-disubstituted 2,5-diketopiperazines by intermolecular condensation of halocarboxamides using a reaction system comprising a mixture of dichloromethane and 50% aqueous sodium hydroxide solution in the presence of a solid phase transfer catalyst. Among the compounds whose syntheses are reported in Okawara et al are 1,4-dibenzylpiperazine-2,5-dione, 1,4-diphenylpiperazine-2,5-dione, and 1,4-diphenyl-3,6-dimethylpiperazine-2,5-dione. The reference does not report any use for the products synthesized.

Cavicchioni et al, "Base-promoted Reactions of α-Halogeno-alkylanilides", *J. Chem. Soc. Perkin Trans. I*, pp. 2969–2972 (1982) reports the preparation of both N,N'-dialkylpiperazines and 2-amino-2-haloalkyloxazolidones by intermolecular condensations of the same reactants used in the syntheses described by Okawara et al. Cavicchioni et al do not give much detail on the reaction system utilized, but apparently employed a polar organic solvent system rather than a two phase system comprising a phase transfer catalyst.

Wong et al U.S. Pat. No. 4,400,330 describes the preparation of bis-phosphonomethyl-2,5-diketopiperazine by phosphonomethylation of 2,5-diketopiperazine, followed by hydrolysis of the bis-phosphonomethyl-2,5-diketopiperazine to produce glyphosate. In the phosphonomethylation, formaldehyde and glacial acetic acid are added to 2,5-diketopiperazine to produce a suspension which is refluxed. Thereafter, phosphorus trichloride is added to the reaction mixture which is then maintained at reflux until all of the hydrogen chloride by-product has been driven off. After additional refluxing of the reaction slurry, the product is dried in vacuo, dissolved in water, and treated sequentially with caustic solution and mineral acid to effect hydrolysis and produce glyphosate.

SUMMARY OF THE INVENTION

Among the several objects of the present invention may be noted the provision of a novel compound useful, inter alia, as an intermediate in the synthesis of glyphosate; the provision of such intermediate which can be converted to glyphosate in relatively high yields; the provision of such a compound which can be conveniently and economically synthesized; and the provision of such an intermediate from which glyphosate can be ecomonically produced.

It is a further object of the invention to provide a novel method for the synthesis of N-isopropylglycine.

Accordingly, the present invention is directed to a novel composition of matter comprising 1,4-diisopropyl-2,5-diketopiperazine. Among other uses, this compound is convertible to various glyphosate precursors and, ultimately, to glyphosate.

The invention is further directed to a process for producing N-isopropylglycine, the method comprising hydrolytically cleaving 1,4-diisopropyl-2,5-diketopiperazine.

DESCRIPTION OF THE PREFERRED EMBODIMENTS

In accordance with the present invention, it has been discovered that 1,4-diisopropyl-2,5-diketopiperazine can be readily and economically synthesized in relatively high yields, and that this compound can be readily converted to glyphosate precursors and, ultimately, to glyphosate. Moreover, it has been found that the synthesis of glyphosate precursors and glyphosate from 1,4-diisopropyl-2,5-diketopiperazine affords exceptionally high yields and is economical to implement and operate.

N,N'-dialkyl-2,5-diketopiperazines may be cleaved hydrolytically to produce the corresponding N-alkylglycine. Using the known method of Moedritzer and Irani (U.S. Pat. No. 3,288,846), the N-alkylglycine may be phosphonmethylated to produce the N-alkyl-N-phosphonomethylglycine (N-alkylglyphosate), which in turn may be dealkylated according to the process of Miller et al, Ser. No. 687,404, filed Dec. 28, 1984, to produce glyphosate. Alternatively, the N,N'-dialkyl-2,5-diketopiperazine may be converted directly to N-alkylglyphosate in accordance with the novel method disclosed in the copending and coassigned application of Miller, Reitz and Pulwer Ser. No. 778,958 filed Sept. 23, 1985.

It has been found that when glyphosate is produced from N-isopropylglyphosate, it is quite feasible to achieve yields in the range of 98%. By comparison, the yields attainable by dealkylation of N-sec-butylglyphosate are about 80%. Yields observed in the dealkylation of other N-alkylglyphosates are lower than those obtained from the isopropyl compound.

Accordingly, it has been found that the novel compound 1,4-diisopropyl-2,5-diketopiperazine provides the starting point for a highly advantageous synthesis of glyphosate. In this respect, the compound of the invention is substantially superior to previously known N,N'-disubstituted-2,5-diketopiperazines, including: 1,4-diethyl-2,5-diketopiperazine, or 1,4-di-n-propyl-2,5-diketopiperazine.

The novel compound of the invention may be prepared by various alternative synthesis schemes. Thus, for example, it may be produced in a manner generally comparable to that described in the Okawara et al article referred to hereinabove. In accordance with this alternative, an α-halo-N-isopropylacetamide and a phase transfer catalyst are dissolved in an organic solvent, a base is added to the mixture, and the reaction is carried out for a time sufficient to effect intermolecular condensation of the α-halo-N-isopropylacetamide. Essentially any conventional organic solvent can be used in this system, provided that it does not react with base or with the α-halo-N-isopropylacetamide. Particularly useful solvents include aromatic solvents such as toluene or xylene, and halogenated solvents such as methylene chloride. If desired, a mixture of solvents (such as a lower boiling alcohol and a halocarbon, plus xylene or toluene) may be used.

Preferably, the base used to effect cyclization comprises an alkali metal hydroxide, most preferably sodium hydroxide. Either solid powdered alkali metal hydroxide or an aqueous solution thereof may be used. However, the use of solid base is preferred since it provides superior yields and conversions while allowing lower proportions of the base to be used. If an aqueous solution is used, it preferably has a strength of at least about 50% by weight. A 50% sodium hydroxide solution is effective for promoting the cyclization reaction, but provides yields and conversions that are significantly lower than those obtained with powdered sodium hydroxide. Increasing the catalyst loading does not compensate for the yield and conversion penalty incurred with the use of as aqueous solution, though increased catalyst loading does increase the rate of the reaction under such conditions. Where powdered sodium or other alkali metal hydroxide is used, it is preferably charged to the reaction in significant excess, i.e., in a proportion of between about 3 and about 3.5 moles, optimally 4–5 moles, per mole of α-halo-N-isopropylacetamide. Where a 50% sodium hydroxide solution is used, it may be necessary to use an excess of up to 10 moles of base per mole of reactant.

The initial concentration of the α-halo-N-isopropylacetamide is not critical but is preferably between about 10% and about 20% by weight based on the organic solvent content of the reaction mixture. Reaction is preferably carried out at moderately elevated temperature, for example, 60° to 100° C., more preferably 65° to 80° C. The amount of phase transfer catalyst utilized is preferably at least about 3 mole percent but not greater than about 10 mole percent based on the initial charge of the α-halo-N-isopropylacetamide.

A variety of conventional phase transfer catalysts can be used to promote the reaction. Preferably the catalyst used is a cationic surfactant such as a quaternary ammonium salt, quaternary phosphonium salt, pyridinium salt, or salt of another heterocyclic base. It is particularly preferred that the phase transfer catalyst be a tetraalkylammonium salt such as tetrapropylammonium chloride, benzyltriethylammonium chloride, tetrabutylammonium hydrogen sulfate, or methyl tricaprylylammonium chloride (Aliquat 336). Nonionic surfactants such as polyethylene glycols of various molecular weights may also be utilized but are not nearly as effective as quaternary ammonium salts in promoting the reaction. Particular polyethylene glycols which may be employed include those sold under the trade designations PEG 400 and 3350 by Union Carbide Corporation.

While the above described phase transfer catalyzed intermolecular condensation comprises an effective method for the preparation of the novel compound of the invention, it is preferred that the compound be prepared by a novel method of Miller and Taylor (attorney's docket No. 2482) involving the condensation of N,N'-diisopropylglycinamide with a haloacetyl halide. In the latter method, the haloacetyl halide, preferably chloroacetyl chloride, is added to a solution of N,N'-diisopropylglycinamide, a hydrogen halide scavenger and an organic solvent. As the haolacetyl halide is added, rapid reaction takes place coupling the haloacetyl halide to the N,N'-diisopropylglycinamide to produce an N-haloacetyl-N,N'-diisopropylglycinamide. A caustic material is then added to effect cyclization to the 1,4-diisopropyl-2,5-diketopiperazine.

Although chloroacetyl chloride is preferred, other haloacetyl halides such as bromoacetyl bromide or choroacetyl bromide may also be used in this reaction. A non-nucleophilic organic base, such as triethylamine, pyridien, or an excess of N,N'-diisopropylglycinamide, is used as the hydrogen halide scavenger. Any organic solvent which is inert to the haloacetyl halide and has a boiling point above the reaction temperature may be used as the medium for the reaction. Preferably hydrocarbon solvents such as toluene or xylene are used.

Prior to and during the addition of haloacetyl halide, the reaction system is preferably maintained at a temperature of not greater than room temperature, more preferably 0° to 15° C., typically by use of an ice bath or refrigeration. Preferably, the N,N'-diisopropylglycinamide, haloacetyl halide and hydrogen halide scavenger are charged to the reaction system in approximately equimolar proportions. However, where an excess of N,N'-diisopropylglycinamide substrate is used as the hydrogen halide scavenger, only about 0.5 mole haloacetyl halide is charged per mole of such substrate. After addition of the haloacetyl halide is complete, the temperature is allowed to rise to room temperature or somewhat above. At this point, a minor proportion of phase transfer catalyst may optionally be added to the reaction system, for example, between about 0.1% and about 3% by weight, based on the amount of N,N'-diisopropylglycinamide in the charge. Thereafter caustic, preferably either naOH or KOH, is added to the reaction mixture to effect cyclization. Either solid powdered caustic or a 50% by weight or greater aqueous solution may be used. Where solid powdered caustic is used, between about 1 and about 2 moles should be charged per mole of product. Where a 50% caustic solution is used, at least about 4 moles should be charged per mole of product. To complete the cyclization, the reaction system is heated to a temperature of between about 65° and about 100° C., preferably between about 75° and about 90° C., typically for 1 to 3 hours.

In the novel process, the product is conveniently recovered by simple phase separation, drying the organic phase, and stripping the solvent. Alternatively, the product may be allowed to remain in the organic phase and the product solution used for further synthesis.

As noted, the novel compound of the invention is useful as an intermediate for the preparation of precursors of glyphosate. Thus, in accordance with the process of the invention, the compound is subjected to hydrolysis in an acid or alkaline, preferably acid, system to produce N-isopropylglycine, which may in turn be phosphonomethylated to N-isopropylglyphosate by sequential reaction with phosphorous acid and formaldehyde according to the method described by Moedritzer and Irani (supra). To carry out the hydrolysis, 1,4-diisopropyl-2,5-diketopiperazine is preferably contacted with an excess mineral acid at an elevated temperature, preferably reflux temperature, i.e., between about 100° and about 105° C. Most preferably, hydrochloric acid having a strength of between about 5% and about 20% by weight is used as the hydrolytic agent. However, other acids, including sulfuric acid and phosphoric acid, or bases may be used.

As noted, N-isopropylglycine obtained from the hydrolysis may be used in the method of Moedritzer and Irani for the preparation of N-ispropylglyphosate. N-isopropylglyphosate may in turn be converted to glyphosate by dealkylation in the presence of base as described in copending and coassigned application of Miller et al, Ser. No. 687,404, filed Dec. 28, 1984.

The 1,4-diisopropyl-2,5-diketopiperazine may be converted directly to N-isopropylglyphosate by the method described in the copending and coassigned application of Miller et al, (attorney's docket No. 2431). In this method the novel compound is phosphonomethylated by reaction with both formaldehyde and phosphorous acid in the presence of a mineral acid, for example, 5–20% hydrochloric acid, without the necessity of isolation of any intermediate reaction product. Again, the N-isopropylglphosate may be converted to glyphosate by the aforesaid process of Miller et al, Ser. No. 687,404, filed Dec. 28, 1984.

The following examples illustrate the invention.

EXAMPLE 1

The compound N-isopropyl-α-chloroacetamide (2.71 g; 0.02 mole) and benzyltriethylammonium chloride (0.09 g) were dissolved in methylene chloride (50 ml) in a 100 ml flask. A 50% by weight sodium hydroxide solution (16 g) was added to the mixture, and the mixture was stirred vigorously at 40° C. for three days. Thereafter, the organic phase was separated, dried and evaporated. The residue of the evaporation (found to be four parts product per part starting material) was recrystallized from ethyl alcohol to yield 0.7 g (36%) of 1,4-diisopropyl-2,5-diketopiperazine. All spectral data were consistent with this structure.

EXAMPLE 2

To a 250 ml Morton flask equipped with a condenser, mechanical stirrer and thermometer were charged 50% sodium hydroxide (48.0 g; 0.60 mole), toluene (60 ml), N-isopropyl-α-chloroacetamide (8.13 g; 0.06 mole), and tetrabutylammonium hydrogen sulfate (0.01 g). The resultant two phase system was vigorously stirred and heated to 80° C. for one hour. The reaction mixture was thereafter diluted with dichloromethane (50 ml) and the caustic layer was separated and extracted with an additional aliquot of dichloromethane (1×25 ml). The organic layers were combined and washed with water (1×25 ml), dried over anhydrous magnesium sulfate and filtered. Solvent was removed under reduced pressure to give a yellow-white solid which was recrystallized from absolute ethanol to give a 3.15 g (53.0% of theoretical) yield of 1,4-diisopropyl-2,5-diketopiperazine as a white crystalline solid, m.p. 177°–180° C. Nuclear magnetic resonance (CDCl$_3$) gave the following results: δ4.75 (septet, 2H, J=7 Hz), 3,80 (s, 4H), 1.15 (d, 12H, J=7Hz). Other analytical results included M.S. parent ion, m/e 198, and elemental analysis for carbon, hydrogen, and nitrogen. The latter analysis showed for C$_{10}$H$_{18}$N$_2$O$_2$:

|   | Calculated | Found |
|---|---|---|
| C | 60.58% | 60.49% |
| H | 9.15 | 9.16 |
| N | 14.13 | 14.10 |

EXAMPLE 3

The 1,4-diisopropyl-2,5-diketopiperazine (0.30 g; 1.5×10$^{-3}$ moles), produced in the manner described in Example 2, concentrated HCl (6 ml), and water (10 ml) were charged to a 50 ml round bottom flask equipped with a condenser and a magnetic stirrer. This mixture was stirred and heated to reflux for 16 hours. An aliquot of the reaction mixture was analyzed by HPLC which showed a 100% yield of N-isopropylglycine.

EXAMPLE 4

The N,N'-diisopropylglycinamide (15.6 g; 0.1 mole), methylene chloride (50 ml), and 50% by weight sodium hydroxide solution (8.0 g; 0.1 mole) were charged to a flask and cooled in an ice bath. Chloracetyl chloride (11.2 g; 0.1 mole) was thereafter added dropwise and the reaction mixture was then allowed to come to room temperature. At this point, benzyltriethylammonium chloride (0.45 g) was added and the reaction mixture was stirred for 1.5 hours. The phases were separated, the organic phase was dried (over calcium chloride), and the volatiles were removed to leave 15.8 g (79.6% yield) of 1,4-diisopropylpiperzine-2,5-dione.

EXAMPLE 5

The compound N,N'-diisopropylglycinamide (7.91 g; 0.05 mole), toluene (70 ml), and triethylamine (5.06 g; 0.05 mole) were charged to a 500 ml Morton flask equipped with a mechanical stirrer, addition funnel and thermometer. The resulting mixture was cooled in an ice bath and 5.6 g (0.05 mole) of chloroacetyl chloride was slowly added dropwise via the addition funnel. After addition of the chloroacetyl chloride was complete, the flask was allowed to warm up to room temperature and stirre for one hour. The flask was then charged with six equivalents (12.0 g; 0.3 mole) of solid powdered sodium hydroxide. The addition funnel was replaced with a condenser, and the reaction mixture was vigorously stirred and heated to 70° C. After the mixture was stirred and heated for 1.5 hours, it was cooled and filtered. The collected solids were washed with dichloromethane. The filtrates and washings were combined and solvent was removed under reduced pressure to give 8.99 g (90.7% of theoretical yield) of 1,4-diisopropyl-2,5-diketopiperazine as a yellow-white solid.

EXAMPLE 6

The compound N,N'-diisopropylglycinamide (7.91 ; 0.05 mol), triethylamine (5.06 g; 0.05 mol), and toulene (70 ml) were charged to a 500 ml Morton flask equipped with a mechanical stirrer and addition funnel. The reaction mixture was cooled in an ice bath and 5.66 g (0.5 mol) of chloroacetyl chloride was slowly added dropwise to the stirred solution. Upon completion of the addition of the chloroacetyl chloride, the ice bath was removed and the flask allowed to warm to room temperature and stirred for about 0.5 hour. A precipitate was observed in the reaction flask. The flask was then charged with a 50% by weight sodium hydroxide solution (24 g) and heated to 70° C. with vigorous stirring. After the mixture was heated and stirred for 1.0 hour, a sample was taken and analyzed by gas chromatography. The results showed 96.3% (area %) of 1,4-diisopropyl-2,5-diketopiperazine with virtually no remaining glycinamide (less than 2.7%).

The reaction mixture was worked up by adding methylene chloride (50 ml), separating off the caustic layer, and washing the caustic layer with an additional aliquot of methylene chloride (1×25 ml). The organic layers were combined, washed with saturated NaCl solution, dried over anhydrous MgSO$_4$, filtered, and the solvent was removed under reduced pressure to give 8.82 g (89%) yield of 1,4-diisopropyl-2,5-diketopiperazine as a pale, yellow-white solid.

EXAMPLE 7

Toluene (50 ml), N,N'-diisopropylglycinamide (3.96 g; 0.025 mol) and triethylamine (2.53 g; 0.025 mol) were charged to a 100 ml round bottom flask that was equipped with a magnetic stir bar and an addition funnel. The flask was cooled to 0°–5° C. in an ice bath and chloroacetyl chloride (2.83 g; 0.025 mol) was added dropwise via the addition funnel. The reaction mixture was then allowed to warm to room temperature and was stirred for 30 minutes. The reaction mixture was then filtered. The filtrates were taken and charged to a 500 ml Morton flask equipped with a thermometer, condenser and mechanical stirrer. Powdered sodium hydroxide (2.0 g; 0.050 mol) was charged to the flask and the reaction mixture was vigorously stirred and heated to 80° C. for one hour. The reaction mixture was then filtered and solvent removed under reduced pressure to give 4.68 g (94.4% yield) of 1,4-diisopropyl-2,5-diketopiperaizne as an off-white solid. The product was recrystallized from ethanol to give a white, crystalline solid having a melting point of 177°–180° C. Analytical results on the product were identical to those obtained in Example 2.

EXAMPLE 8

Toluene (75 ml), N-sec-butyl-2-chloracetamide (14.9 g, 0.10 mol), tetrabutylammonium hydrogen sulfate (1.7 g, 5×10$^{-3}$ mol), and powdered sodium hydroxide (16.0 g, 0.40 mol) were charged into a 500 ml Morton flask equipped with a mechanical stirrer, thermometer and condenser. The reaction mixture was vigorously stirred and heated to 75° C. for one hour. The reaction mixture was cooled, filtered and solvent removed under reduced pressure. The resulting solids were recrystallized from ether to give 7.0 g (62%) of 1,4-di-sec-butyl-2,5-diketopiperazine as an off-white colored solid, mp 95.5°–97.5° C. Analytical results on the product were as follows: $^1$H NMR (CDCl$_3$, TMS, 90 MHz) δ4.54 (septet, J=7 Hz, 2H), 3.78 (s, 4H), 1.45 (q, J=6 Hz, 4H), 1.10 (d, J=6 Hz, 6H), 0.83 (t, J=7 Hz, 6H) Mass spectrum, m/e =226 (parent). Anal. calcd. for C$_{12}$H$_{22}$N$_2$O$_2$:C, 63.68; H, 9.80; N, 12.38. Found: C, 63,51; H, 9.82; N, 12.30.

In view of the above, it will be seen that the several objects of the invention are achieved and other advantageous results attained.

As various changes could be made in the above methods and products without departing from the scope of the invention, it is intended that all matter contained in the above description or shown in the accompanying drawings shall be interpreted as illustrative and not in a limiting sense.

What is claimed is:

1. The compound 1,4-diisopropyl-2,5-diketopiperazine.

* * * * *